(12) United States Patent
Sugihara et al.

(10) Patent No.: US 10,335,071 B2
(45) Date of Patent: Jul. 2, 2019

(54) PHYSIOLOGICAL PARAMETER MEASURING APPARATUS AND PHYSIOLOGICAL PARAMETER MEASURING SYSTEM

(71) Applicant: NIHON KOHDEN CORPORATION, Shinuku-ku, Tokyo (JP)

(72) Inventors: Norihiko Sugihara, Tokyo (JP); Kazumasa Ito, Tokyo (JP); Osamu Kamataki, Tokyo (JP); Hiroko Hagiwara, Tokyo (JP); Rie Muneshima, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 263 days.

(21) Appl. No.: 15/281,485

(22) Filed: Sep. 30, 2016

(65) Prior Publication Data
US 2017/0100065 A1  Apr. 13, 2017

(30) Foreign Application Priority Data

Oct. 7, 2015 (JP) .................................. 2015-199716

(51) Int. Cl.
*A61B 5/1455* (2006.01)
*G16H 40/20* (2018.01)
(Continued)

(52) U.S. Cl.
CPC .......... *A61B 5/14551* (2013.01); *A61B 5/024* (2013.01); *A61B 5/02416* (2013.01);
(Continued)

(58) Field of Classification Search
CPC .................. A61B 5/14551; A61B 5/7435
See application file for complete search history.

(56) References Cited

U.S. PATENT DOCUMENTS

2005/0020898 A1   1/2005  Vosniak et al.
2006/0206356 A1*  9/2006  Vanderveen ........ A61M 5/1407
                                                           705/2
(Continued)

FOREIGN PATENT DOCUMENTS

JP    2001-175775    6/2001
JP    2004-49309     2/2004
JP    2015-523883    8/2015

OTHER PUBLICATIONS

Communication dated Mar. 17, 2017, issued by the European Patent Office in counterpart European application No. 16191891.7.
(Continued)

*Primary Examiner* — Thaddeus B Cox
(74) *Attorney, Agent, or Firm* — Sughrue Mion, PLLC (57) ABSTRACT

A physiological parameter measuring apparatus is configured to perform a screening for a likelihood of the critical congenital heart disease, based on the oxygen saturations at two locations on a body of a patient and the difference between the oxygen saturations, and to display the likelihood as a result of the screening. The physiological parameter measuring apparatus manages, with respect to each patient, a scheduled time for starting the screening, the result of the screening, and information relating to the patient. The physiological parameter measuring apparatus can display a first screen containing information relating to the scheduled time, a second screen for receiving the instruction to perform the screening, and a third screen containing the result of the screening. A physiological parameter measuring system includes sensors to be attached to the body at the two locations, and the physiological parameter measuring apparatus.

9 Claims, 8 Drawing Sheets

(51) Int. Cl.
*A61B 5/024* (2006.01)
*A61B 5/00* (2006.01)
*G16H 40/63* (2018.01)
*G16H 50/30* (2018.01)

(52) U.S. Cl.
CPC ........ *A61B 5/14557* (2013.01); *A61B 5/7282* (2013.01); *A61B 5/743* (2013.01); *A61B 5/7435* (2013.01); *A61B 5/7475* (2013.01); *G16H 40/20* (2018.01); *G16H 40/63* (2018.01); *G16H 50/30* (2018.01); *A61B 2503/04* (2013.01); *A61B 2503/045* (2013.01)

(56) References Cited

U.S. PATENT DOCUMENTS

| | | |
|---|---|---|
| 2013/0190581 A1 | 7/2013 | Al-Ali et al. |
| 2013/0331634 A1* | 12/2013 | Kaintz ............... A61M 39/223 600/4 |
| 2013/0331635 A1 | 12/2013 | Hoffman et al. |
| 2013/0331691 A1 | 12/2013 | Uber, III et al. |
| 2013/0331801 A1 | 12/2013 | Hoffman et al. |
| 2014/0135603 A1 | 5/2014 | Boyer et al. |
| 2015/0112171 A1 | 4/2015 | Chang |
| 2015/0150513 A1 | 6/2015 | Kobayashi et al. |
| 2015/0254412 A1 | 9/2015 | Humphrys et al. |
| 2015/0328446 A1 | 11/2015 | Kaintz et al. |
| 2015/0374914 A1 | 12/2015 | Uber, III et al. |
| 2016/0331998 A1 | 11/2016 | Hoffman et al. |

OTHER PUBLICATIONS

Japanese Patent Office, Communication issued Apr. 23, 2019, in copending Japanese Application No. 2015-199716.

* cited by examiner

| PATIENT ID | NAME | DATE AND TIME OF BIRTH | NEXT SCREENING TIME | FINISHED SCREENIG | |
|---|---|---|---|---|---|
| 100004 | NOAH WILLIAMS | 10-01 13:01 | 10-02 15:01 | ■■☐ | ▲ |
| 100005 | JOHN SMITH | 10-01 14:10 | 10-02 15:10 | ■☐☐ | |
| 100006 | EMMA JONES | 10-02 09:20 | 10-03 09:20 | ☐☐☐ | |
| 100007 | JACKSON DAVIS | 10-02 11:35 | 10-03 11:35 | ☐☐☐ | |
| 100008 | MICK SCHENKER | 10-02 12:05 | 10-03 12:05 | ☐☐☐ | |
| 100009 | KEVIN CUTHBERT | 10-02 12:15 | 10-03 12:15 | ☐☐☐ | |
| 100010 | MARY FOX | 10-02 12:40 | 10-03 12:40 | ☐☐☐ | |
| 100011 | SARAH FORSTER | 10-02 13:05 | 10-03 13:05 | ☐☐☐ | ▼ |

2014-10-02 14:30

NEW PATIENT

| PATIENT ID, NAME, DATE AND TIME OF BIRTH | SCREENING TIME | SpO2 | | | JUDGE | FINAL JUDGE |
|---|---|---|---|---|---|---|
| | | RH | F | Δ | | |
| 100002<br>EMILY WILSON<br>10-01-2014 11:01 | 10-02 11:01 | 98 | 94 | 4 | FAIL | P |
| | 10-02 12:01 | 98 | 95 | 3 | PASS | |
| 100001<br>PETER SCOFIELD<br>10-01-2014 10:10 | 10-02 10:10 | 98 | 94 | 4 | FAIL | P |
| | 10-02 11:10 | 98 | 94 | 4 | FAIL | |
| | 10-02 12:10 | 98 | 96 | 2 | PASS | |
| 100003<br>THOMAS FINN<br>10-01-2014 11:15 | 10-02 11:15 | 94 | 90 | 4 | FAIL | F |
| | 10-02 12:15 | 94 | 89 | 5 | IMMIDIATE FAIL | |

2014-10-02 14:30

16

17 P  18 F  19 –

20 ONE PRINT  21 MULTI PRINT  22 MULTI USB

FIG. 9

PHYSIOLOGICAL PARAMETER MEASURING APPARATUS AND PHYSIOLOGICAL PARAMETER MEASURING SYSTEM

CROSS-REFERENCE TO RELATED APPLICATION(S)

The present application claims priority from Japanese Patent Application No. 2015-199716 filed on Oct. 7, 2015, the entire content of which is incorporated herein by reference.

BACKGROUND

The presently disclosed subject matter relates to a physiological parameter measuring apparatus and a physiological parameter measuring system.

Since congenital heart disease in a neonate often threatens the life, it is very important to early detect such disease. In a medical institution such as a hospital treating neonates, therefore, screenings for critical congenital heart diseases (CCHDs) are performed. A related art screening method is based on a measurement of an arterial oxygen saturation (SpO2) of a neonate.

US2013/0190581 A1 discloses a method for CCHD screening, and a pulse oximeter for performing the screening method. In the screening method, SpO2 at a right hand finger and SpO2 at a toe are measured by pulse oximeters, and screening for the likelihood of CCHD is performed based on the difference of the measured SpO2s. The measurement results of the SpO2s at the right hand finger and the toe, and a result of the CCHD screening are displayed on the screen of a display disposed in the pulse oximeter. Based on the result of the screening, the medical person determines whether a further examination such as echocardiogram is to be performed.

With this related art pulse oximeter, CCHD screening for one person may be performed promptly. However, a large hospital, a hospital for obstetrics, or the like treats a large number of neonates. Screening is performed a plurality of times at time intervals. In the case of a plurality of neonates, therefore, a probe of a pulse oximeter must be replaced. In such a case, a medical person needs to manage the sequence of the neonates who are to undergo screening, also to perform screening by using a pulse oximeter and to transcribe the results to medical records. When looking into the result of past screening of a specific neonate, the medical person needs to check the medical record of the neonate. In this kind of conventional procedure for the screening method, machine dependent steps and human and paper document dependent steps are mixed. Therefore, cumbersome works are required, and a large burden is placed on the medical person.

SUMMARY

Illustrative aspects of the presently disclosed subject matter provide a physiological parameter measuring apparatus and a physiological parameter measuring system allowing a medical person to conduct a CCHD screening with a reduced burden.

According to a first aspect of the presently disclosed subject matter, a physiological parameter measuring apparatus is configured to perform a screening for critical congenital heart disease. The physiological parameter measuring apparatus includes an acquiring section, a calculating section, a judging section, a controller, and a display. The acquiring section is configured to acquire a first oxygen saturation at a first portion of a body of a patient and a second oxygen saturation at a second portion of the body, the second portion being different from the first portion. The calculating section is configured to calculate a difference between the first oxygen saturation and the second oxygen saturation. The judging section is configured to perform, upon receipt of an instruction to perform the screening, and based on the first and second oxygen saturations and the difference, the screening for a likelihood of the critical congenital heart disease with respect to the patient, and to output the likelihood as a result of the screening. The controller is configured to manage, with respect to each patient, a scheduled time for starting the screening, the result of the screening, and information relating to the patient. The display is configured to receive an input by an operator, and to display, in a switchable manner, a first screen containing information relating to the scheduled time, a second screen for receiving the instruction to perform the screening, and a third screen containing the result of the screening.

According to a second aspect of the presently disclosed subject matter, a physiological parameter measuring system includes the physiological parameter measuring apparatus described above, a first sensor configured to be attached to the first portion of the body, and a second sensor configured to be attached to the second portion of the body. The acquiring section is configured to acquire the first oxygen saturation and the second oxygen saturation, based on measurement signals from the first and second sensors.

According to a third aspect of the presently disclosed subject matter, a control program controls the physiological parameter measuring apparatus. The control program causes a computer to execute a method includes steps of (a) managing a scheduled time for starting the screening for each patient and displaying the scheduled time, (b) accepting an instruction to perform the screening, (c) acquiring a first oxygen saturation at a first portion of a body of the patient and a second oxygen saturation at a second portion of the body, the second portion being different from the first portion, and calculating a difference between the first oxygen saturation and the second oxygen saturation, (d) performing the screening for a likelihood of the critical congenital heart disease with respect to the patient, based on the first and second oxygen saturations and the difference, and (e) displaying a result of the screening. The control program may be stored in a non-transitory computer readable medium.

DETAILED DESCRIPTION

Hereinafter, exemplary embodiments of the presently disclosed subject matter will be described with reference to the accompanying drawings. In the figures, the same components are denoted by the same reference numerals. In the drawings, the dimension ratios may be exaggerated for the purpose of illustration, and may be sometimes different from the actual ratios.

Figure 1:
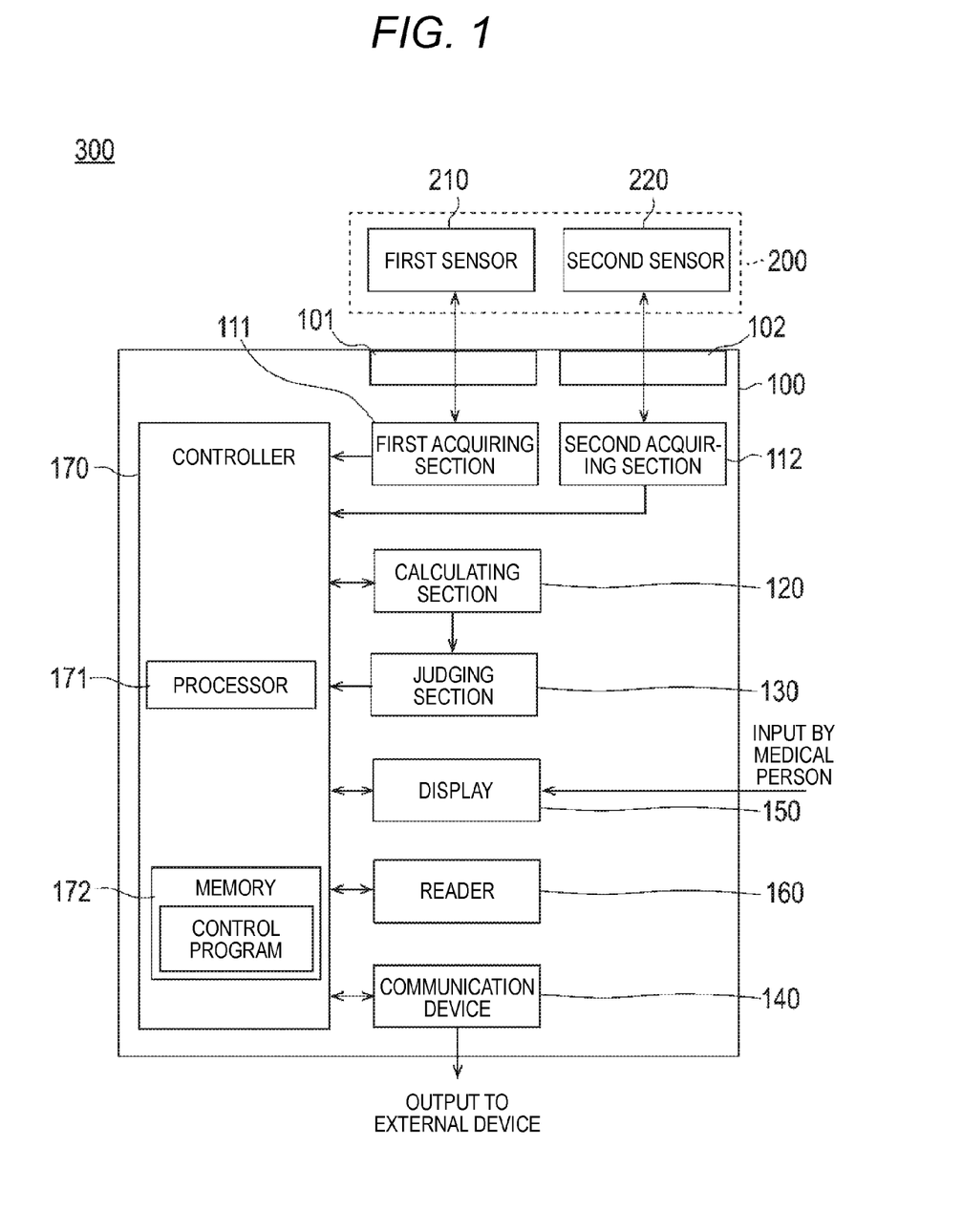
FIG. 1 is a block diagram schematically illustrating a configuration of a physiological parameter measuring system according to an exemplary embodiment of the present invention.
Figure 2:
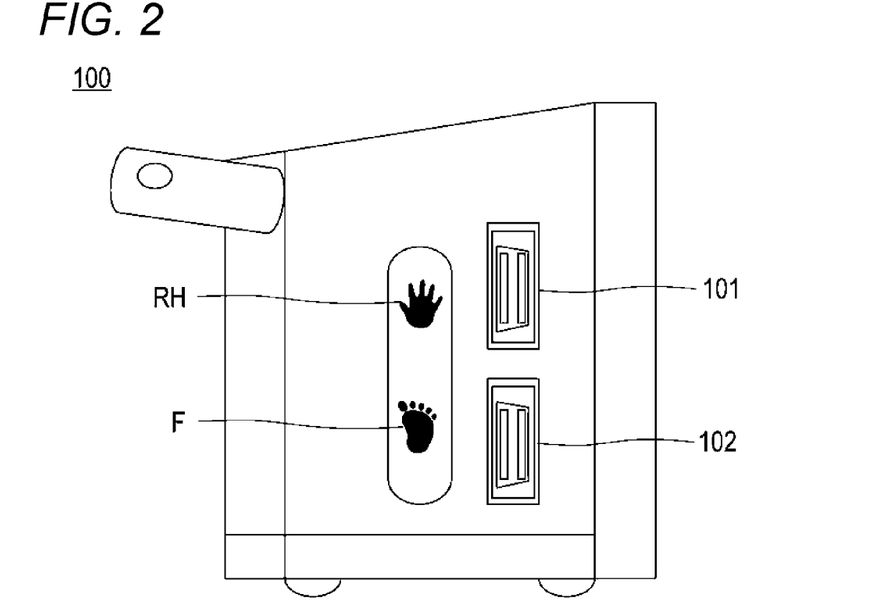
FIG. 2 is a side view of a physiological parameter measuring apparatus of the system of FIG. 1.
Figure 3:
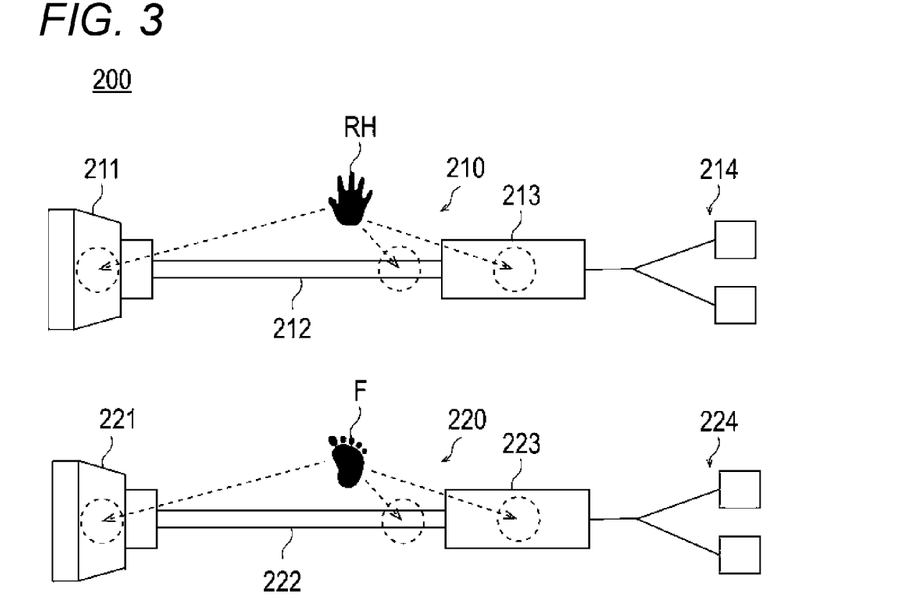
FIG. 3 is a diagram illustrating first and second sensors of the system of FIG. 1.

FIG. 1 is a block diagram schematically illustrating a configuration of a physiological parameter measuring system 300 according to an exemplary embodiment of the present invention. FIG. 2 is a side view of a physiological parameter measuring apparatus 100 illustrated in FIG. 1, and FIG. 3 is a plan view of first and second sensors 210, 220 illustrated in FIG. 1.

As illustrated in FIG. 1, the physiological parameter measuring system 300 can include the physiological parameter measuring apparatus 100 and a sensor section 200. The physiological parameter measuring apparatus 100 can include a first connector 101, a second connector 102, a first acquiring section 111, a second acquiring section 112, a calculating section 120, a judging section 130, a communication device 140, a display 150, a reader 160, and a controller 170. The physiological parameter measuring apparatus 100 is a pulse oximeter having, for example, a 2-channel sensor input. The sensor section 200 can include a first sensor 210 and a second sensor 220.

The first and second connectors 101, 102 are connectors for connecting the first and second sensors 210, 220 to the first and second acquiring sections 111, 112, respectively.

The first and second acquiring sections 111, 112 acquire arterial oxygen saturations of two portions of the body of the patient undergoing screening, respectively. More specifically, the first acquiring section 111 acquires a first arterial oxygen saturation in the right hand (first portion) of the patient, and the second acquiring section 112 acquires a second arterial oxygen saturation in the foot (second portion). In the exemplary embodiment, the first sensor 210 is attached to the right hand of the patient, and the second sensor 220 is attached to the foot of the patient. The first and second acquiring sections 111, 112 calculate the first and second arterial oxygen saturations based on measurement signals from the first and second sensors 210, 220, respectively. The first and second acquiring sections 111, 112 may be controlled by a processor not shown in the drawings. The second sensor 220 may be attached to either the right or left foot.

As illustrated in FIG. 2, on the side surface of the housing of the physiological parameter measuring apparatus 100 (the main unit of the physiological parameter measuring system 300), a mark (indication) RH of "Hand" is provided near the first connector 101, and a mark (indication) F of "Foot" is provided near the second connector 102. The marks RH, F may be printed on the surface of the housing at locations corresponding to the first and second connectors 101, 102, respectively.

As illustrated in FIG. 3, the first sensor 210 can include a first cable connector 211, a first cable 212, a first relay unit 213, and a first probe 214. The second sensor 220 can include a second cable connector 221, a second cable 222, a second relay unit 223, and a second probe 224.

In the first sensor 210, for example, a mark (indication) RH of "Hand" is provided on at least one of the first cable connector 211, the first cable 212, and the first relay unit 213. The mark RH may be printed on at least one of the surfaces of the first cable connector 211, the first cable 212, and the first relay unit 213.

In the second sensor 220, for example, a mark (indication) F of "Foot" is provided on at least one of the second cable connector 221, the second cable 222, and the second relay unit 223. The mark F may be printed on at least one of the surfaces of the second cable connector 221, the second cable 222, and the second relay unit 223.

In the physiological parameter measuring system 300 of the exemplary embodiment, as described above, the hand or foot mark is drawn on the first and second sensors 210, 220, and also in the connecting portions which are in the physiological parameter measuring apparatus 100, and which are used in connection with the first and second sensors 210, 220, respectively. Therefore, the medical person can connect the first and second sensors 210, 220 to the physiological parameter measuring apparatus 100 while checking correspondence relationships between the hand or foot mark of the first and second sensors 210, 220 and that of the physiological parameter measuring apparatus 100. Therefore, it is possible to prevent erroneous connection between the first and second sensors 210, 220 and the physiological parameter measuring apparatus 100, from occurring.

The first probe 214 is attached to the right hand of the patient. The first probe 214 can include a light emitter and a light detector. The light emitter emits a red light beam and an infrared light beam. The light detector detects the red light beam and infrared light beam transmitted through or reflected from the right hand of the patient, and outputs a first measurement signal corresponding to the intensities of the detected red and infrared light beams. The first measurement signal is supplied to the first acquiring section 111 through the first cable 212.

The second probe 224 is attached to the foot of the patient. The second probe 224 can include a light emitter and a light detector. The light emitter emits a red light beam and an infrared light beam. The light detector detects the red light beam and infrared light beam which are transmitted through or reflected from the foot of the patient, and outputs a second measurement signal corresponding to the intensities of the detected red and infrared light beams. The second measurement signal is supplied to the second acquiring section 112 through the second cable 222.

The first acquiring section 111 acquires a temporal change of the light attenuation ratio in the right hand of the patient, based on the first measurement signal front the first sensor 210, and calculates the first arterial oxygen saturation in the right hand of the patient based on the temporal change of the light attenuation ratio.

The second acquiring section 112 acquires a temporal change of the light attenuation ratio in the foot of the patient, based on the second measurement signal from the second sensor 220, and calculates the second arterial oxygen saturation in the foot of the patient based on the temporal change of the light attenuation ratio.

The method for calculating the SpO2 from the light attenuation ratio is a known technique, and therefore its description is omitted.

The calculating section 120 calculates the difference between the first arterial oxygen saturation and the second arterial oxygen saturation. The calculated difference is supplied to the judging section 130. The calculating section 120 further calculates the pulse rate (PR) based on the first and second measurement signals. Moreover, the calculating section 120 calculates the signal quality indices (SQIs) as a level of reliability of the first and second measurement signals, and evaluates the reliabilities of the first and second measurement signals based on whether or not the corresponding SQI is equal to or greater than a predetermined value.

The judging section 130 performs screening for the likelihood of CCHD with respect to the patient, based on the first and second artery oxygen saturations, and the difference. The judgement result of the CCHD screening is supplied as a screening result to the controller 170. The function of the judging section 130 will be described in detail later.

The communication device 140 transmits various kinds of information stored in the controller 170, to an external device which is not shown. When the judging section 130 judges a result of CCHD screening with respect to a certain specific patient as positive, the communication device 140 provides the result of CCHD screening to an external facility via a network in accordance with instructions from the controller 170. Therefore, a plurality of physiological parameter measuring apparatuses including the physiological parameter measuring apparatus 100 can provide screening results to the external facility, and the results can be aggregated.

The display 150 may include a touch panel, and has a function of receiving an input from a medical person (an operator), and a function of displaying various kinds of information stored in the controller 170. Information input by a medical person is transmitted to the controller 170. The display 150 is configured to display, in a switchable manner, a screen first screen) containing information relating to a scheduled time for starting the screening for each patient, a screen (a second screen) on which an instruction from a medical person to perform the screening is input, and a screen (a third screen) containing a result of the screening of each patient. The "scheduled time" may be "a scheduled point of time" and/or "a period of time until the scheduled point of time." In the following example, for the purpose of illustration, the "scheduled time" refers to "the scheduled point of time".

The reader 160 reads identification information indicated on a tag of each patient. A tag is attached to each of patients. The tag includes an identifier containing identification information specific to the patient. For example, the reader 160 is a bar code reader, and configured so as to be able to read a bar code which is identification information. The identification information which is read by the reader 160 is transmitted to the controller 170.

The controller 170 may include a processor 171 and a memory 172 (an example of a non-transitory computer readable medium). The processor 171 executes various programs, including a control program, stored in the memory 172, to control the calculating section 120, the judging section 130, the communication device 140, the display 150, and the reader 160. The memory 172 stores also various kinds of information such as scheduled times when screenings for the patients are to be started, screening results, and information of the patients. The controller 170 manages the various kinds of information, and as required transmits the information to the communication device 140 and the display 150.

The controller 170 may verify the identification of the patient by checking the identification information read by the reader 160 with the patient identification information registered in the memory 172.

Figure 4:
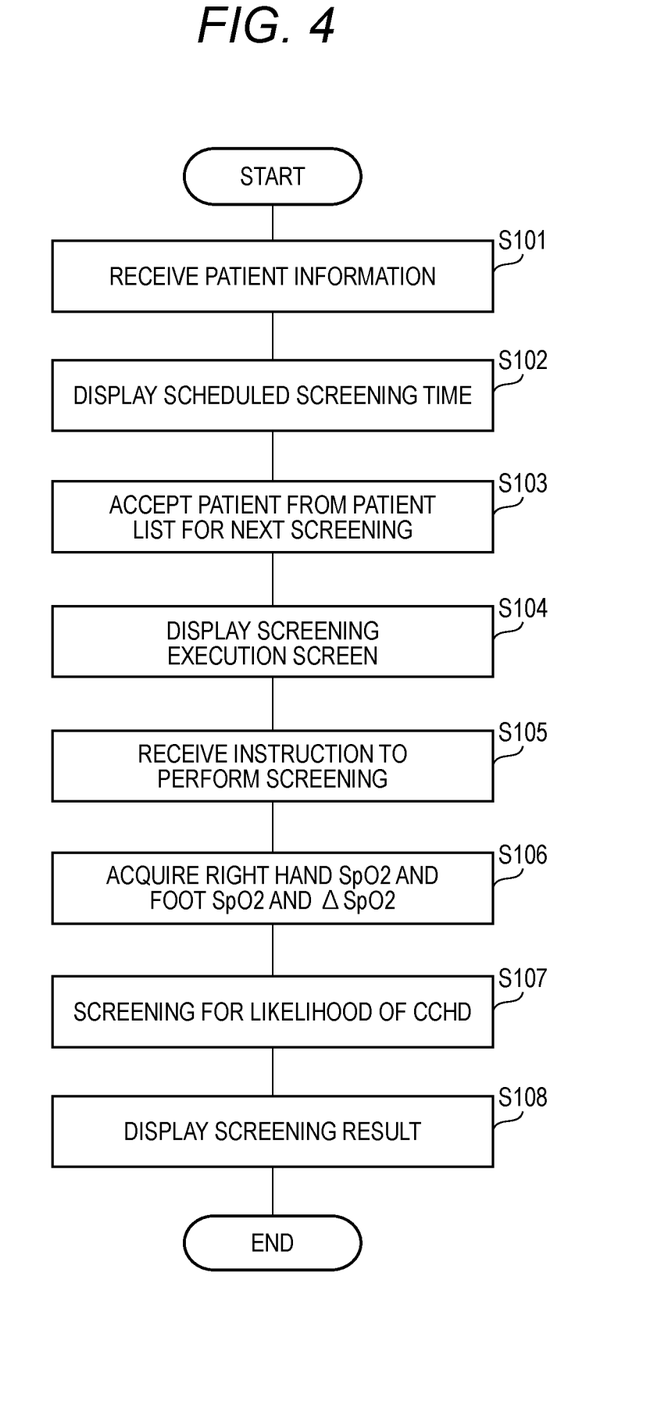
FIG. 4 is a flowchart of an example of a method for controlling the physiological parameter measuring apparatus.
Figure 5:
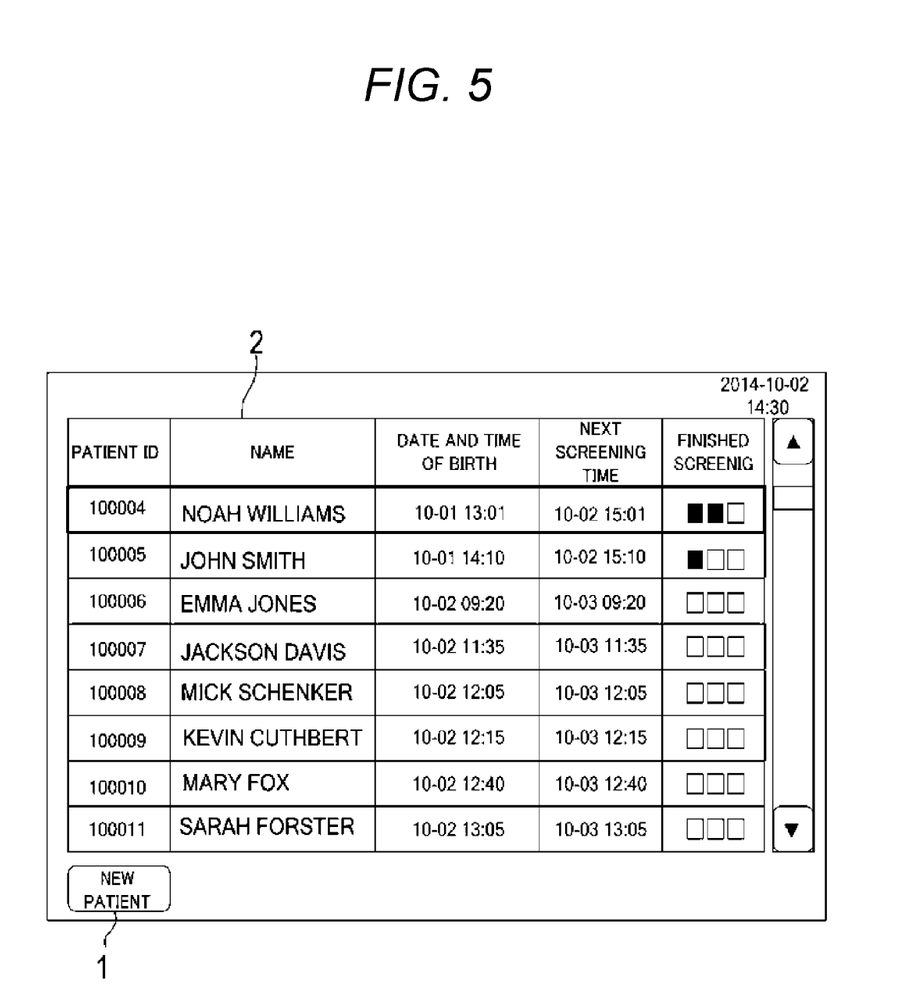
FIG. 5 is a diagram illustrating an example of "PATIENT SELECTION SCREEN"
Figure 6:
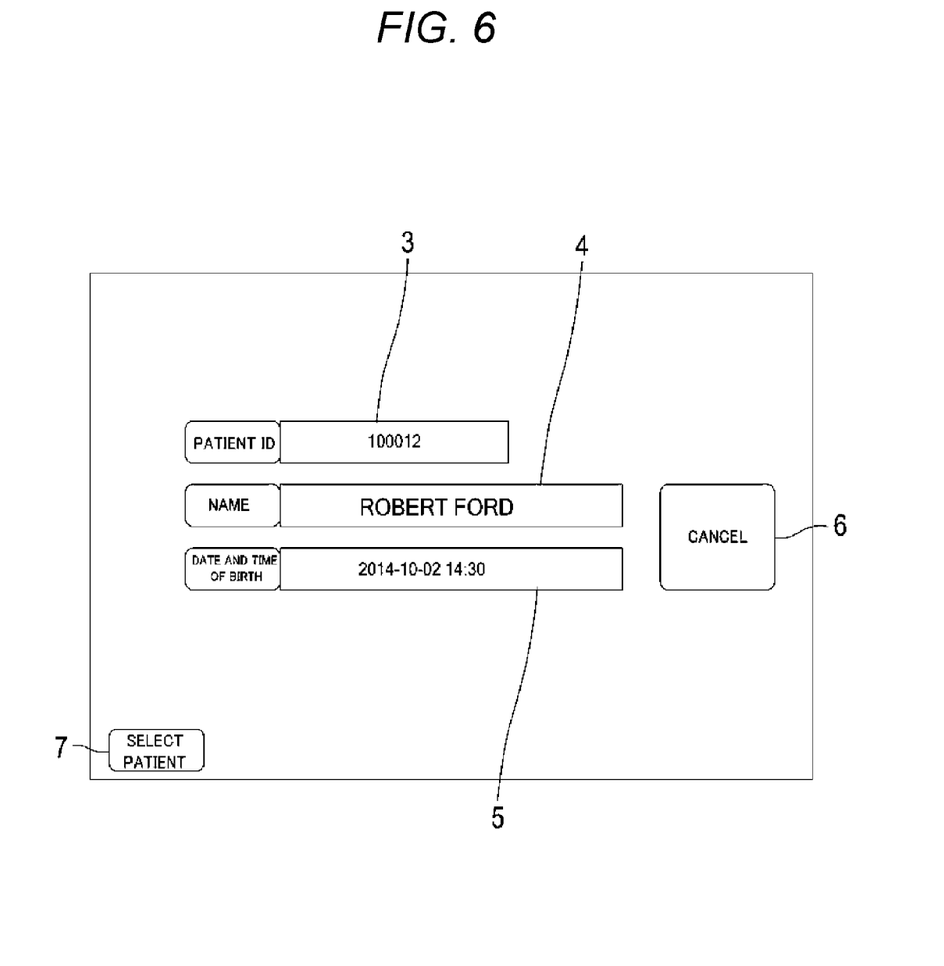
FIG. 6 is a diagram illustrating an example of "PATIENT INFORMATION SCREEN"
Figure 7:
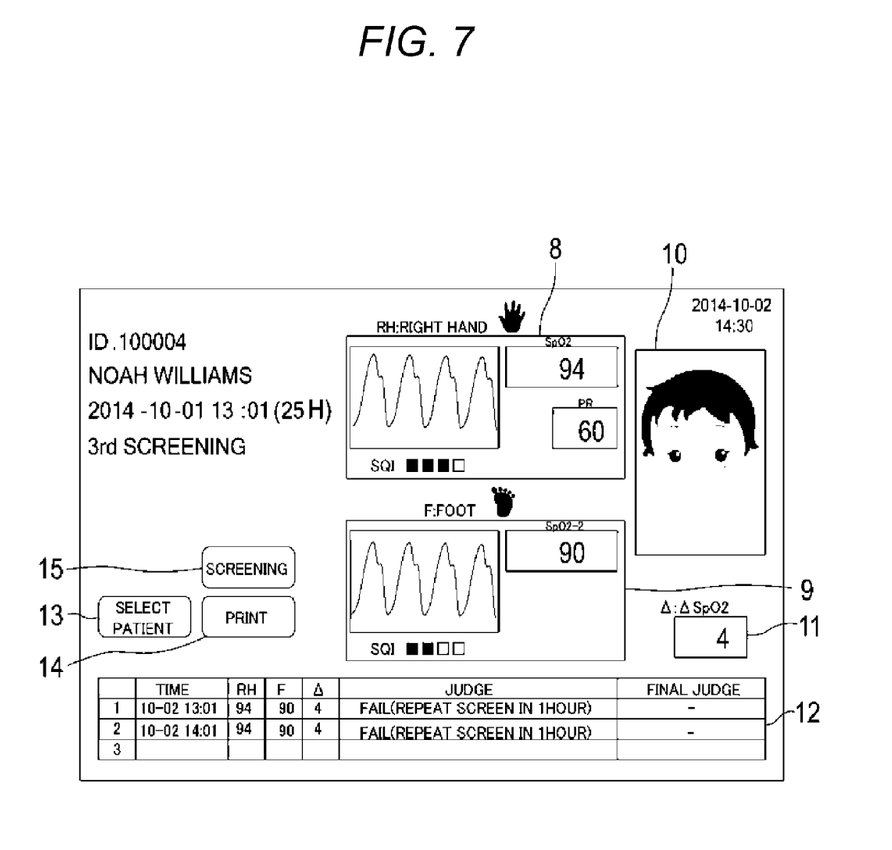
FIG. 7 is a diagram illustrating and example of "EXECUTION SCREEN"
Figure 8:
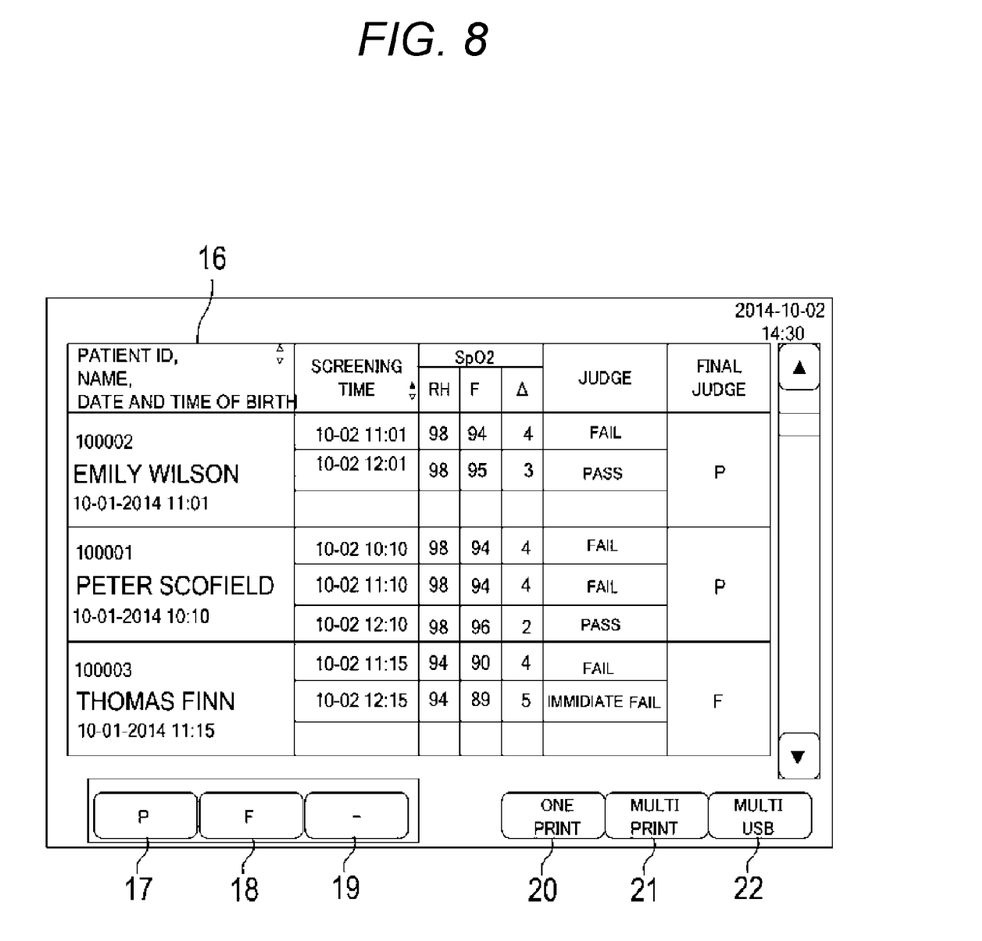
FIG. 8 is a diagram illustrating an example of "REPORT DISPLAY SCREEN"

Hereinafter, a method for controlling the physiological parameter measuring apparatus 100 will be described in detail with reference to FIGS. 4 to 8. FIG. 4 is a flowchart of an example of the method for controlling the physiological parameter measuring apparatus 100 illustrated in FIG. 1, FIG. 5 is a diagram illustrating an example of "PATIENT SELECTION SCREEN", FIG. 6 is a diagram illustrating an example of "PATIENT INFORMATION SCREEN", FIG. 7 is a diagram illustrating an example of "EXECUTION SCREEN", and FIG. 8 is a diagram illustrating an example of "REPORT DISPLAY SCREEN". The method for controlling the physiological parameter measuring apparatus 100 is implemented when the controller 170 executes the control program.

First, information relating to a patient is received (step S101). In "PATIENT SELECTION SCREEN" (first screen) illustrated in FIG. 5, a medical person touches a "NEW PATIENT" button located in the lower left area, and then "PATIENT INFORMATION SCREEN" is displayed (see FIG. 6). On "PATIENT INFORMATION SCREEN," as illustrated in FIG. 6, the identification number ("PATIENT ID"), name ("NAME"), and date and time of birth ("DATE AND TIME OF BIRTH") of the new patient are input. The identification number is input into an identification number input region 3, the name is input into a name input region 4, and the date and time of birth are input into a date and time of birth input region 5. In the example of FIG. 6, "100012" is input as the identification number, "ROBERT FORD" is input as the name, and 14:30 of Oct. 2, 2014 is input as the date and time of birth.

In the controller 170, a screening queue of patients who are to undergo screening is held in the memory 172. Input information is stored in the memory 172 as the information relating to the patient, and registered in the screening queue.

A "CANCEL" button 6 is used for interrupting screening for the patient in whom information has been input, without executing the whole screening process. When a "SELECT PATIENT" button 7 is touched, the process can return to above-described "PATIENT SELECTION SCREEN."

Alternatively, the information of the identification number, the name, and the date and time of birth may be previously stored in the form of a bar code on the tag of a new patient, and, when the information is read by a bar code reader, the information of the identification number, name, and date and time of birth of the new patient may be input.

Next, the scheduled screening time is displayed (step S102). In the screening queue, sets of information relating to patients who are scheduled to undergo screening are registered in ascending order of the scheduled screening time. As illustrated in FIG. 5, the controller 170 refers the screening queue, and causes a screen including a list 2 of patients who are to undergo screening, to be displayed on the display 150, thereby prompting the medical person to select the patient who is to next undergo screening.

In the patient list 2, "PATIENT ID" indicates the identification number of a patient, "NAME" indicates the name, "DATE AND TIME OF BIRTH" indicates the date and time of birth, "NEXT SCREENING TIME" indicates the scheduled time for the next screening, and "FINISHED SCREENING" indicates the number of finished screenings. With respect to the number of finished screenings, in order to enable the medical person to easily visually understand the number of finished screenings, finished screening and not-finished screening are expressed by "■" (solid square) and "□" (blank square) respectively. The current date and time (14:30 of Oct. 2, 2014) are displayed on the upper right side of "PATIENT SELECTION SCREEN."

For example, information of a patient in whom the identification number is "100004," the name is "NOAH WILLIAMS," the date and time of birth are "13:01 of October 1," the scheduled time for the next screening is "15:01 of October 2," and the number of finished screenings is two is displayed in the top row of the patient list 2.

The display order in the patient list 2 may be sorted by using "PATIENT ID," "NAME," "DATE AND TIME OF BIRTH," "NEXT SCREENING TIME," and "FINISHED SCREENING" as sort keys. With respect to "PATIENT ID" and "NEXT SCREENING TIME," it is possible to select an ascending sort or a descending sort.

In the exemplary embodiment, the patient list 2 is sorted when the screen is switched to "PATIENT SELECTION SCREEN" from another screen. As a result, at least part of information relating to the patients is displayed in the order of the scheduled time for the next screening. In the example illustrated in FIG. 5, "NOAH WILLIAMS" is scheduled to earliest undergo screening, and, as a result of sorting. "NOAH WILLIAMS" is displayed in the top row of the patient list 2, "NOAH WILLIAMS" is therefore displayed while enclosed by thick lines. This means that the patient is scheduled to be earliest subjected to screening. Therefore, the medical person can surly recognize the next patient to undergo screening.

Next, a patient who is to next undergo screening is accepted from the patient list 2 (step S103). When the medical person touches "PATIENT SELECTION SCREEN," the medical person selects the patient who is to next undergo screening, from the patient list 2. When the medical person touches the region enclosed by the thick lines, for example, the controller 170 accepts "NOAH WILLIAMS" as the patient who is to next undergo screening.

Next, a screening execution screen is displayed (step S104). The controller 170 controls the display 150 so as to display "EXECUTION SCREEN" (the second screen) for performing screening for patient "NOAH WILLIAMS" (see FIG. 7). In a case in which another patient displayed in the patient list 2 on "PATIENT SELECTION SCREEN" is touched in step S103, "EXECUTION SCREEN" for performing screening for the other patient is displayed.

Next, an instruction to perform the screening is received (step S105). As illustrated in FIG. 7, the identification number, name, date and time of birth (total time from birth), and number of screenings of the patient who is selected in step S103 are displayed in the upper left area of "EXECUTION SCREEN." In the example illustrated in FIG. 7, it is displayed that the identification number is "100004," the name of the patient is "NOAH WILLIAMS," the date and time of birth are 13:01 of Oct. 1, 2014 (the total time from birth: 25 hours, and the screening is the third screening.

A first measurement display region 8 for "RIGHT HAND" in "EXECUTION SCREEN" includes a pulse wave display region, an SQI display region, an SpO2 display region, and a pulse rate display region. In the first measurement display region, the pulse wave, SQI, SpO2, and pulse rate of the right hand in which the measurement is currently advancing are displayed in real time. The value of the SQI is indicated by the number of "■" (solid square). The character string "RH: RIGHT HAND" and the image indicating "hand" clearly show that the first measurement display region 8 is a region where the pulse wave, SQI, SpO2, and pulse rate of the right hand are displayed.

A second measurement display region 9 for "FOOT" includes a pulse wave display region, an SQI display region, and an SpO2 display region. In the second measurement display region, the pulse wave, SQI, and SpO2 of the foot in which the measurement is currently advancing are displayed in real time. The character string "F: FOOT" and the image indicating "foot" clearly show that the second measurement display region 9 is a region where the pulse wave, SQI, and SpO2 of the foot are displayed.

When, as described above, the pulse wave. SpO2, and pulse rate of the patient are displayed in real time, the medical person can promptly address an abnormal condition of the patient or a sudden change of the condition. Although, in the example illustrated in FIG. 7, the pulse rate of the foot is not displayed, also the pulse rate of the foot can be displayed as required.

An image display region 10 and a difference display region 11 are placed in the right side of "EXECUTION SCREEN." An image (image object) of a neonate is displayed in the image display region 10, and the difference between the SpO2s of the right hand and the foot (hereinafter, the difference is referred to as "ΔSpO2") is displayed in the difference display region 11.

The exemplary embodiment is configured so that the image of a neonate is, for example, an illustration of a neonate, and the facial expression (shape) of the illustrated neonate is changed in accordance with the screening result. More specifically, the illustration is changed to one in which the facial expression is different, in accordance with the screening result. Alternatively, a configuration may be employed where, in place of an illustration of a neonate, an image of a neonate itself who is a patient may be used, and the shape of the image is changed in accordance with the screening result. Not only the shape of the image, but also the color or contrast of the image may be changed. As described above, the shape of an image of a neonate which is displayed on "EXECUTION SCREEN" is changed in accordance with the result of the screening, and therefore the medical person can easily see the result of the screening.

A result display region 12 is placed in the lower portion of "EXECUTION SCREEN." In the result display region 12, "TIME" indicates the time when screening was performed, "RH" indicates the SpO2 (first arterial oxygen saturation) of the right hand, "F" indicates the SpO2 (second arterial oxygen saturation) of the foot, "Δ" indicates the ΔSpO2, "JUDGE" indicates a judgement result, and "FINAL JUDGE" indicates a final judgement result. In the example illustrated in FIG. 7, it is scheduled that screening will be performed three times, and results of first and second screenings which have been already performed are displayed. For example, it is shown that the first screening was performed at 13:01 of October 2, the SpO2 of the right hand is "94," the SpO2 of the foot is "90," ΔSpO2 is "4," and the judgement result is "FAIL (screening is performed within one hour)."

The arrangement of the first measurement display region 8, the second measurement display region 9, the image display region 10, the difference display region 11, and the result display region 12 is not limited to the above-described one. The arrangement may be adequately changed in consideration of convenience of use by the medical person.

"EXECUTION SCREEN" further includes a "SELECT PATIENT" button 13, a "PRINT" button 14, and a "SCREENING" button 15. The "SELECT PATIENT" button 13 is a button for returning to "PATIENT SELECTION SCREEN" illustrated in FIG. 5, and the "PRINT" button 14 is a button for printing "EXECUTION SCREEN." The "PRINT" button 14 may be set as to be enabled only when the result of the first screening is displayed in the result display region 12.

The "SCREENING" button 15 is a button for starting the screening. The "SCREENING" button 15 is enabled when a screening accepting condition is satisfied, but is disabled when the screening accepting condition is not satisfied. In a state in which the "SCREENING" button 15 is enabled, when a medical person touches the "SCREENING" button 15, the controller 170 accepts an instruction to perform the screening. The "SCREENING" button 15 is grayed out when it is disabled, and the controller 170 does not accept an instruction to perform the screening. This function may be turned on and off by setting.

The screening accepting condition may include the reliabilities of the first and second measurement signals, and identification of the patient who is to undergo screening. When the reliabilities (SQIs) of the first and second measurement signals are equal to or greater than a predetermined value, the controller 170 and the display 150 enable an input of an instruction to performing the screening in "EXECUTION SCREEN." When the reliability of one of the first and second measurement signals is smaller than the predetermined value, an input of an instruction to perform screening in "EXECUTION SCREEN" is disabled. Therefore, the screening can be performed after the reliabilities of the measurement signals of the first and second sensors are confirmed.

The controller 170 may be configured to determine whether the identification information of the patient who is to next undergo screening matches the identification information acquired by reading, the bar code of the tag attached to the patient by the bar code reader, and to accept the instruction to perform the screening only it matches. With this configuration, the screening is performed after the patient who is to next undergo screening is identified, and therefore the screening can be surely performed on the patient who is to undergo screening. Furthermore, the patient who is to undergo screening can surely undergo screening.

When the first and second measurement signals are unstable and therefore their reliabilities cannot be ensured, for example, a message such as "wait until signals become stable" may be displayed on "EXECUTION SCREEN." Although not illustrated, an input key (button) for canceling the registration of the screening queue may be provided in "EXECUTION SCREEN."

Upon instruction to perform the screening, the controller 170 updates the scheduled time for the next screening of the patient who is undergoing the screening, and the order in the screening queue.

Next, the SpO2s of the right hand and the foot, and the ΔSpO2 are acquired (step S106). When the SpO2 measurement is started, the first and second acquiring sections 111, 112 measure the SpO2s of the right hand and the foot in real time, respectively, and therefore the measurement values of the SpO2s of the right hand and the foot change over time. The calculating section 120 calculates the ΔSpO2 in real time based on the acquired SpO2s of the right hand and the foot. When the medical person touches the "SCREENING" button 15 and screening is started, the first and second acquiring sections 111, 112 hold the outputs of the SpO2s to determine and acquire the SpO2s of the right hand and foot of the patient, respectively. The calculating section 120 calculates and acquires the ΔSpO2 based on the SpO2s of the right hand and the foot which are acquired by the first and second acquiring sections 111, 112.

Next, screening for the likelihood of CCHD is performed (step S107). The judging section 130 performs screening for the likelihood of CCHD based on the acquired SpO2s of the right hand and the foot, and the ΔSpO2. The method for judging CCHD screening will be specifically described later.

When the final judgement result of the screening is already output with respect to the patient, the controller 170 deletes information relating to the patient from the screening queue in the memory 172.

Next, the result of screening is displayed (step S108). The controller 170 reflects to the SpO2s of the right hand and the foot, the ΔSpO2, and a judgement result of CCHD screening on recording of screening results of the patient. In the case where "EXECUTION SCREEN" is displayed, the controller 170 causes the screening result to be displayed in the result display region 12. Moreover, the medical person can check the screening result of the patient to whom the final judgement result is output, on "REPORT DISPLAY SCREEN."

As illustrated in FIG. 8, "REPORT DISPLAY SCREEN" (third screen) displays a result list 16 of screening results of patients to whom the final judgement result is output. In the result list 16, "PATIENT ID" indicates the identification number of a patient, "NAME" indicates the name, and "DATE AND TIME OF BIRTH" indicates the date and time of birth. "SCREENING TIME" indicates the time when screening was performed, "RH," "F," and "Δ" in the column of SpO2 indicate the SpO2 of the right hand, the SpO2 of the foot, and the ΔSpO2, respectively, "JUDGE" indicates a judgement result of each screening, and "FINAL JUDGE" indicates a final judgement result.

In the example illustrated in FIG. 8, it is displayed that "EMILY WILSON" underwent first screening at 11:01 of October 2, the SpO2s of the right hand and the foot are "98" and "94," respectively, the ΔSpO2 is "4," and the judgement result is "FAIL." Moreover, it is displayed that the patient underwent second screening at 12:01 of October 2, the SpO2s of the right hand and the foot are "98" and "95," respectively, the ΔSpO2 is "3," and the judgement result is "PASS." Furthermore, it is displayed that the final judgement result of "EMILY WILSON" is "P (PASS)."

The display order in the result list 16 can be sorted by using "PATIENT ID" or "SCREENING TIME" as a sort key. In the sort using "PATIENT ID" or "SCREENING TIME," it is possible to select an ascending sort or a descending sort.

In the example illustrated in FIG. 8, with respect to the patients in whom the final judgement result is "P" or "F," the screening result is displayed. When the medical person touches a "P" button 17 in "REPORT DISPLAY SCREEN," only the screening result(s) of a patient(s) in whom the final judgement result is "P" is displayed. When the medical person touches an "F" button 18, only the screening result(s) of a patient(s) in whom the final judgement result is "F" is displayed. When the medical person touches a "–" button 19, a patient(s) in whom a "CANCEL" button 6 was pressed during screening and the screening was interrupted is displayed.

In "REPORT DISPLAY SCREEN," when a "ONE PRINT" button 20 is touched, the screening result of each patient can be printed, and, when a "MULTI PRINT" button 21 is touched, the screening results of a plurality of patients who satisfy predetermined conditions are printed at one time. For example, the predetermined conditions include that the final result was obtained within a designated time range. When a "MULTI USB" button 22 is used, the screening results of a plurality of patients can be stored in a bundle in another device through a USB, or stored in a USB memory.

Basically, screening results displayed in the result list 16 are not deleted. With respect to screening results which have been stored in another device by using the "MULTI USB" button 22, however, the screening results can be deleted from the result list 16.

According to the method for controlling the physiological parameter measuring apparatus 100 as illustrated in the flowchart of FIG. 4, information relating to each patient is received, a scheduled time for the screening is displayed, and the patient who is to next undergo screening is input from the patient list 2. Next, the screening execution screen is displayed, and after accepting an instruction to perform the screening, the SpO2s at the right hand and the foot and ΔSpO2 are acquired to perform the screening for the likelihood of CCHD of the patient. Then, a result of the screening is displayed.

In the method for controlling the physiological parameter measuring apparatus 100, the order of displaying the screens is not limited to the example of FIG. 4. When operating the touch screen of the display 150, the medical person can cause "PATIENT SELECTION SCREEN," "EXECUTION SCREEN," "PATIENT INFORMATION SCREEN," and "REPORT DISPLAY SCREEN" to be selectively displayed in a switchable manner.

Alternatively, at the scheduled time when next screening is to be performed, or immediately before arrival of the scheduled time, the medical person may be informed of the arrival of the scheduled time. For example, the controller 170 may cause a message indicating arrival of the scheduled time to be displayed in a partial region of "PATIENT SELECTION SCREEN," "EXECUTION SCREEN," "PATIENT INFORMATION SCREEN," or "REPORT DISPLAY SCREEN," or inform of the arrival by a sound, an alarm, or the like.

Figure 9:
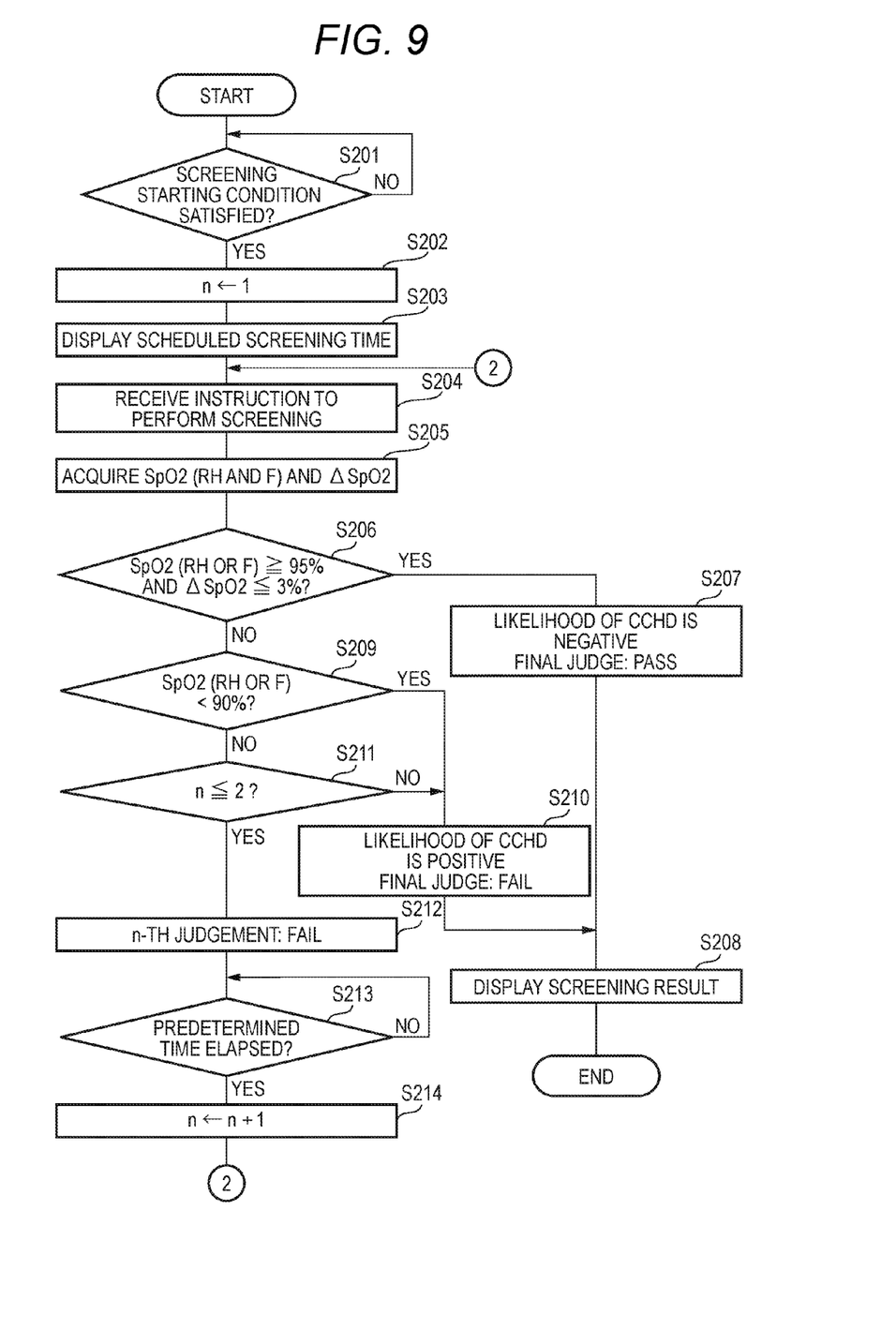
FIG. 9 is a flowchart of an example of a method for judging CCHD.

FIG. 9 is a flowchart illustrating an example of a method for judging CCHD. The method for judging CCHD in the exemplary embodiment is based on the CCHD screening protocol recommended by the U.S. Centers for Disease Control and Prevention.

First, it is determined whether the conditions for starting the screening are satisfied. (step S201). In the case where the patient is a normal neonate, the judging section 130 starts the screening after 24 hours or more from the birth except in special circumstances. The time period from the birth of the patient and to the start of screening may be set optionally by the medical person. The default time period is 24 hours.

Next, "n" as set as 1 (step S202). Here, "n" is a counter for counting the number of screenings.

Next, the scheduled time for the screening is displayed (step S203). With respect to each of patients who are to undergo screening, the controller 170 manages and displays the scheduled time for starting the screening. The medical person selects the patient who is to next undergo screening, through the display 150.

Next, an instruction to perform the screening is received (step S204). On "EXECUTION SCREEN," the medical person touches the "SCREENING" button 15 to instruct to perform the screening on the selected patient, and the controller 170 accepts the instruction to perform the screening.

Next, the SpO2s of the right hand and the foot, and the ΔSpO2 are acquired (step S205). When screening is started, the first and second acquiring sections 111, 112 hold the outputs of the SpO2s to determine and acquire the SpO2s of the right hand and the foot, respectively. The calculating section 120 calculates and acquires the ΔSpO2 based on the SpO2s of the right hand and the foot which are acquired by the first and second acquiring sections 111, 112, respectively.

Next, it is determined whether or not the SpO2 of the right hand or the foot is 95% or more and whether or not the ΔSpO2 is 3% or less (step S206). If the SpO2 of the right hand or the foot is 95% or more and the ΔSpO2 is 3% or less (step S206: YES), the likelihood of CCHD is negative, and the final judgement result is set as "PASS" (step S207).

Next, the result of screening is displayed (step S208). The controller 170 updates the record of screening results of the patient which is stored in the memory 172. In the case where "EXECUTION SCREEN" is displayed, the controller 170 causes the screening result to be displayed in the result display region 12. When the medical person switches to "REPORT DISPLAY SCREEN," the controller 170 causes the result list 16 of screening results of patients to whom the final judgement result is output. Then, the process is ended (END).

If the SpO2 of the right hand or the foot is not 95% or more and the ΔSpO2 is not 3% or less (step S206: NO), it is determined whether the SpO2 of the right hand or the foot is smaller than 90% or not (step S209). If the SpO2 of the right hand or the foot is smaller than 90% (step S209: YES), the judgement result is "IMMEDIATE FAIL." In this case, the likelihood of CCHD is positive, and the final judgement result is set as "FAIL" (step S210), and then the process transfers to step S208. In the case where the likelihood of CCHD is positive, a more detailed examination is necessary.

If the SpO2 of the right hand or the foot is not smaller than 90% (step S209: NO), it is determined whether or not "n" is equal to or smaller than 2 (step S211). If "n" is not equal to or smaller than 2, i.e., in the case of third screening (step S211: NO), the likelihood of CCHD is positive, the final judgement result is set as "FAIL," and the process transfers to step S208. If "n" is equal to or smaller than 2, i.e., in the case of first or second screening (step S211: YES), the n-th judgement result is set as "FAIL," and the record of screening results of the patient is updated (step S212).

Next, it is determined whether a predetermined time period has elapsed (step S213). For example, the predetermined time period is one hour. The predetermined time period may be changed as appropriate by the medical person.

Next, "n" is incremented by 1 (step S214). To the counter for counting the number of screenings, 1 is added, and the process transfers to step S204.

The thresholds of the SpO2 of the right hand, SpO2 of the foot, and ΔSpO2 at which the judgement result or the final judgement result is set to "PASS," "FAIL," or "IMMEDIATE FAIL" can be changed by the medical person as required.

Also the maximum number of screenings which can be performed can be changed by the medical person as required.

The physiological parameter measuring apparatus 100 and physiological parameter measuring system 300 which have been described above achieve the following effects.

The physiological parameter measuring apparatus 100 manages and displays the scheduled time for starting the screening for each patient who are to undergo screening. Therefore, a medical person can easily recognize the patients who are waiting for the screening. A result of the screening can be stored in the physiological parameter measuring apparatus 100. Therefore the medical person is not required to transcribe the result of the screening to medical records.

Moreover, the physiological parameter measuring apparatus 100 can manage and display information relating to patients and past screening results. Therefore, the medical person can easily view the past screening results of a specific patient. Consequently, the physiological parameter measuring apparatus 100 can avoid cumbersome works in conventional screening. When CCHD screening is to be performed, therefore, the burden on a medical person can be reduced.

The physiological parameter measuring system 300 can achieve, with respect to each of patient, the management of the scheduled time for starting the screening, performing the screening, and display of past screening results in one system. When CCHD screening is to be performed, therefore, cumbersome works in conventional screening can be avoided, and hence the burden on the medical person can be reduced.

While the present invention has been described with reference to certain exemplary embodiments thereof, the scope of the present invention is not limited to the exemplary embodiments described above, and it will be understood by those skilled in the art that various changes and modifications may be made therein without departing from the scope of the present invention as defined by the appended claims.

For example, an input from a medical person may be received through an input device other than the touch panel, such as a mouse or a keyboard.

The verification of identification may not be performed as a screening accepting condition at the time of receiving an instruction to perform the screening. For example, the selection of the patient may be performed by verifying the identity of the patient using identification information on the tag of the patient, instead of touching "PATIENT SELECTION SCREEN" by the medical person, but also by performing identification based on identification information indicated on the tag of the patient. Alternatively, the verification of identification may be performed at a different timing Further, instead of reading the bar code on the tag attached to the patient, the verification of identification may be performed by reading an IC tag attached to the patient through wireless communication.

What is claimed is:

1. A physiological parameter measuring apparatus for performing a screening for critical congenital heart disease, the apparatus comprising:
    a first sensor configured to be attached to a first portion of a body of a patient;
    a second sensor configured to be attached to a second portion of the body, the second portion being different from the first portion;
    a memory storing computer-readable instructions; and
    a processor configured to execute the computer-readable instructions, which when executed cause the processor to control the physiological parameter measuring apparatus to:
        control acquisition of a first oxygen saturation at the first portion and a second oxygen saturation at the second portion of the body, based on measurement signals from the first sensor and the second sensor;
        control calculation of a difference between the first oxygen saturation and the second oxygen saturation;
        upon receipt of an instruction to perform the screening, and based on the first and second oxygen saturations and the difference, control performance of the screening for a likelihood of the critical congenital heart disease with respect to the patient, and to output the likelihood as a result of the screening;
        control management of, with respect to each patient, a scheduled time for starting the screening, the result of the screening, and information relating to the patient; and
        control a display configured to receive an input by an operator, to display, in a switchable manner, a first screen including a list of patients and containing information relating to the scheduled time for starting the screening for each patient, a second screen for receiving the instruction to perform the screening, and a third screen containing the result of the screening,
        wherein the first sensor has an indication of a hand or a foot,
        wherein the second sensor has an indication of the hand or the foot that is not indicated on the first sensor, and
        wherein the physiological parameter measuring apparatus has indications corresponding to the indications of the hand and the foot on the first and second sensors, at portions where the first and second sensors are connected respectively.

2. The physiological parameter measuring apparatus according to claim 1, wherein the processor, when the computer-readable instructions are executed, controls the physiological parameter measuring apparatus to manage the scheduled time for a next screening of each patient, and
    controls the display to display, on the first screen, at least part of the information relating to each patient in an order of the scheduled time for the next screening of each patient.

3. The physiological parameter measuring apparatus according to claim 1, wherein the processor, when the computer-readable instructions are executed, controls the display to display, on the second screen, an image object having a shape that changes in accordance with the result of the screening.

4. The physiological parameter measuring apparatus according to claim 1,
    wherein the processor, when the computer-readable instructions are executed, controls the physiological parameter measuring apparatus to calculate a reliability of measurement signals from the first sensor and a reliability of measurement signals from the second sensor, and
    controls the display to enable to accept the instruction to perform the screening on the second screen when the reliabilities of the measurement signals from the first and second sensors are both equal to or greater than a predetermined value.

5. The physiological parameter measuring apparatus according to claim 1, further comprising a reader configured to read a tag that is attached to each patient, the tag including an identifier containing identification information specific to the patient,
    wherein the processor, when the computer-readable instructions are executed, controls the physiological parameter measuring apparatus to accept the instruction to perform the screening from the second screen only when identification information of a patient who is scheduled to next undergo the screening matches the identification information acquired by reading the identifier of the tag attached to the patient by the reader.

6. The physiological parameter measuring apparatus according to claim 1, wherein the processor, when the computer-readable instructions are executed, controls the physiological parameter measuring apparatus to transmit via a network the result of the screening to an external device when the screening result is positive.

7. A physiological parameter measuring system of performing a screening for critical congenital heart disease, the system comprising:
   a first sensor configured to be attached to a first portion of a body of a patient;
   a second sensor configured to be attached to a second portion of the body, the second portion being different from the first portion; and
   a physiological parameter measuring apparatus, wherein the physiological parameter measuring apparatus comprises:
      a memory storing computer-readable instructions; and
      a processor configured to execute the computer-readable instructions, which when executed cause the processor to control the physiological parameter measuring apparatus to:
         control acquisition of a first oxygen saturation at the first portion and a second oxygen saturation at the second portion, based on measurement signals from the first sensor and the second sensor;
         control calculation of a difference between the first oxygen saturation and the second oxygen saturation;
         upon receipt of an instruction to perform the screening, and based on the first and second oxygen saturations and the difference, control performance of the screening for a likelihood of the critical congenital heart disease with respect to the patient, and to output the likelihood as a result of the screening;
         control management of, with respect to each patient, a scheduled time for starting the screening, the result of the screening, and information relating to the patient; and
         control a display configured to receive an input performed by an operator, to display, in a switchable manner, a first screen containing information relating to the scheduled time, a second screen for receiving the instruction to perform the screening, and a third screen containing the result of the screening,
   wherein the first sensor has an indication of a hand or a foot,
   wherein the second sensor has an indication of the hand or the foot that is not indicated on the first sensor, and
   wherein the physiological parameter measuring apparatus has indications corresponding to the indications of the hand and the foot on the first and second sensors, at portions where the first and second sensors are connected respectively.

8. The physiological parameter measuring system according to claim 7, wherein the processor, when the computer-readable instructions are executed configured to control the display to display, on the first screen, at least part of the information relating to each patient in an order of the scheduled time for a next screening of each patient.

9. The physiological parameter measuring system according to claim 7, wherein the processor, when the computer-readable instructions are executed configured to control the display to display, on the second screen, an image object having a shape that changes in accordance with the result of the screening.

* * * * *